United States Patent [19]
Brezoczky et al.

[11] Patent Number: 5,661,559
[45] Date of Patent: Aug. 26, 1997

[54] OPTICAL SURFACE DETECTION FOR MAGNETIC DISKS

[75] Inventors: Blasius Brezoczky; Vladimir Pogrebinsky, both of San Jose, Calif.

[73] Assignee: Phase Metrics, Inc., San Diego, Calif.

[21] Appl. No.: 616,103

[22] Filed: Mar. 14, 1996

[51] Int. Cl.⁶ .................................................. G01B 9/02
[52] U.S. Cl. ........................ 356/353; 356/359; 356/374
[58] Field of Search ................................. 356/345, 353, 356/357, 359, 360, 374

[56] References Cited

U.S. PATENT DOCUMENTS

| | | | |
|---|---|---|---|
| 3,218,916 | 11/1965 | Saunders | 356/353 |
| 4,794,550 | 12/1988 | Greivenkamp | 356/357 |
| 4,948,251 | 8/1990 | Kondo | 356/359 |

*Primary Examiner*—Samuel A. Turner
*Attorney, Agent, or Firm*—Blakely, Sokoloff, Taylor & Zafman

[57] ABSTRACT

An automatic surface inspection apparatus comprises a light source that provides a coherent light beam that is spit and then recombined in a prism to generate an interference pattern. A cylindrical lens projects the interference pattern onto the surface of a disk as a line of light. A linear detection array converts the reflected line of light into an electrical signal that has a magnitude which varies dependent upon the reflected light intensity. Defects present on the surface of the disk cause variations in the reflected light intensity manifested as differences in the electrical signal output by the detection array.

28 Claims, 2 Drawing Sheets

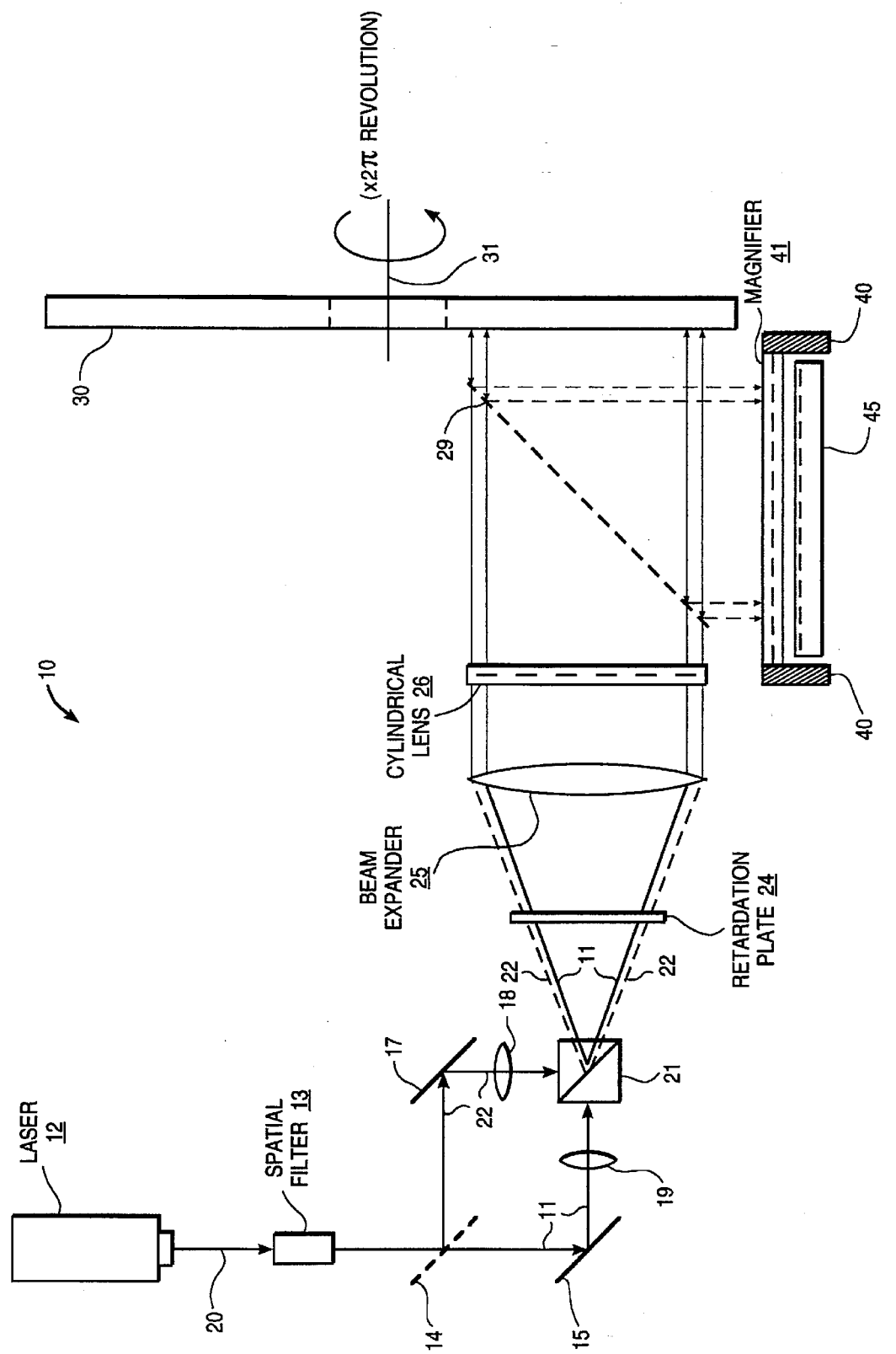
FIG_1

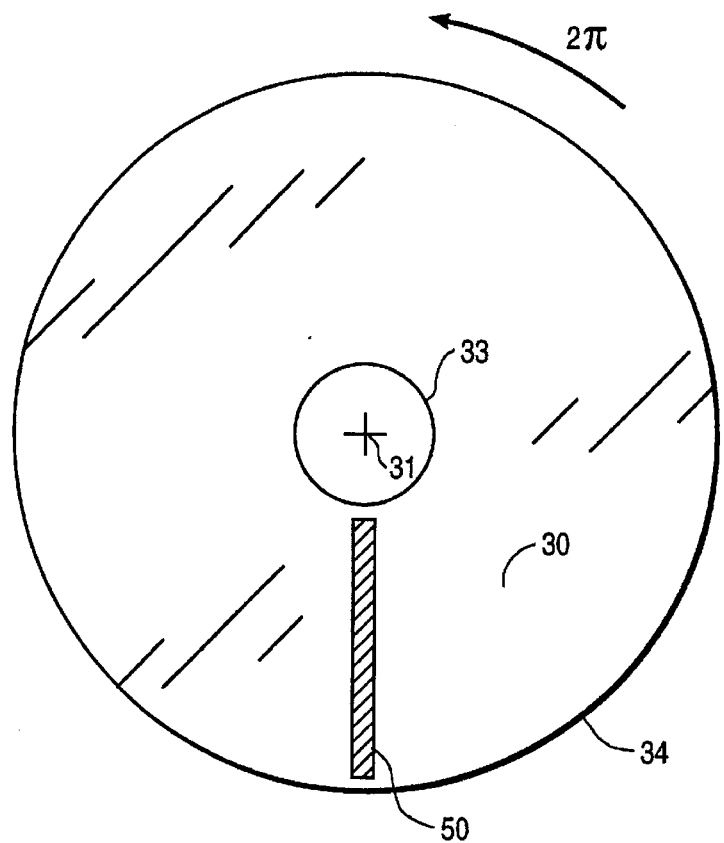
FIG_2
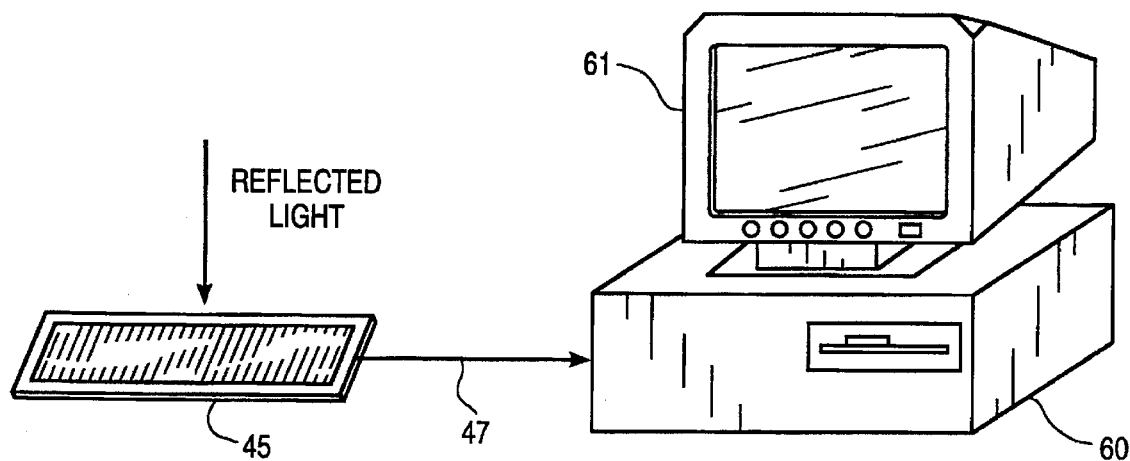
FIG_3

OPTICAL SURFACE DETECTION FOR MAGNETIC DISKS

FIELD OF THE INVENTION

The present invention relates generally to the field of magnetic disks. More specifically, the invention relates to apparatus and techniques for inspecting the surface of a magnetic disk for defects and the like.

BACKGROUND OF THE INVENTION

Disk drive magnetic recording is accomplished by the relative motion between a magnetic head and a magnetic medium. In a disk drive system, the magnetic medium typically comprises a circular rigid disk having a magnetic material incorporated or embedded into its surface. As the disk is rotated, a hydrodynamic air film develops between the magnetic head and the surface of the magnetic medium. Thus, the magnetic head is said to "fly" above the surface of the disk. In state-of-the-art disk drive units, flying heights are on the order of one microinch above the surface of the disk.

The low flying heights commonly found in modern disk drive systems mandate that the magnetic disks themselves be manufactured to have ultra-smooth surfaces. Unfortunately, during the manufacturing process, the magnetic recording surface may be inadvertently damaged. Alternatively, contaminate particles introduced in the manufacturing process can end up causing imperfections on the disk surface. These imperfections can adversely affect the way the head flies. For example, a rough surface texture with numerous defects projecting above the planar surface of the disk can cause destructive head crashes. Conversely, pits or voids in the recording surface may result in a loss of magnetic information—even without interfering with the flying characteristics of the slider or head.

Because of the critical requirement for an ultra-smooth disk surface, manufacturers of magnetic recording disks must devote considerable time to certifying the surface characteristics of the magnetic disk. Typically, this involves a visual inspection of the disk's surface for defects. It is desirable to both qualify and quantify the type, as well as the location, of imperfections present on the surface of the recording medium. To avoid problem areas during recording, there is also a need to map the entire disk surface so as to be able to locate defects and identify their type. If the number and/or type of defects exceeds acceptable tolerances, the entire disk may be rejected. By way of example, if a particular defect is very large and protrudes above the surface of the disk, the disk might be rejected.

As will be seen, the present invention provides an apparatus and method for optically inspecting the surface of magnetic disks. According to the invention, defects and problem areas are pinpointed with an optical detection apparatus capable of differentiating between various types of defects. The invention also satisfies the need for an inspection tool that provides both qualitative and quantitative analysis of the disk's surface. The inspection apparatus is highly accurate and provides a simple, cost-effective method for certifying magnetic disks.

SUMMARY OF THE INVENTION

The present invention covers an apparatus and method for detecting defects and imperfections on the surface of a magnetic disk. In one embodiment the invention is implemented as an automatic surface inspection tool that is capable of qualifying and quantifying defects on the magnetic disk surface. The disk surface may comprise a bare substrate material, or alternatively, a finished magnetic disk.

The inspection apparatus comprises a light source that provides a single wavelength light beam. After spitting the light beam into separate components, an ordinary optical cube or prism is utilized to generate an interference pattern. A cylindrical lens projects the interference pattern onto the surface of the magnetic disk as a line of light. The linear light pattern is projected such that it extends radially across the disk's surface, i.e., from an inside diameter to an outside diameter of the disk. A linear detection array is employed to convert the reflected line of light into an electrical signal. The electrical signal has a magnitude that varies dependent upon the reflected light intensity.

The invention operates on the principle that defects present on the surface of the magnetic disk cause variations in the reflected light intensity. These variations are manifested as differences in the electrical signal output by the detector array. A computer or similar data processing device may be advantageously employed to digitally map the size, location and type of defects present on the disk's surface.

The type of the defect may be determined by further including a means for moving the photo detector array along an axis that is substantially parallel to the reflection of the line of light. Moving the photo detector array in this direction varies the optical distance between the photo detector array and the surface of the magnetic disk. Moving the array in this manner allows the inspection apparatus to differentiate the type of defect that is present on the disk's surface. That is, the apparatus is capable of differentiating between protrusions (i.e., bumps) or holes.

By slowly turning the magnetic disk a full revolution (i.e., $2\pi$) about its central rotational axis, the reflection of the interference pattern may be detected over an annular area of the recording surface—the area being bounded by the inside and outside diameters of the disk. In this manner, the entire magnetic recording surface can be mapped from a single revolution of the disk. Furthermore, the optical apparatus of the present invention is extremely accurate: capable of detecting defects less than 0.5 microns wide.

BRIEF DESCRIPTION OF THE DRAWINGS

The present invention will be understood more fully from the detailed description which follows and from the accompanying drawings, which, however, should not be taken to limit the invention to the specific embodiments shown, but rather are provided for explanation and understanding only.

FIG. 1 is a conceptual diagram of the inspection apparatus of the present invention.

FIG. 2 is a front view of a magnetic disk under inspection according to one embodiment of the present invention.

FIG. 3 illustrates an embodiment of the present invention in which a linear detection array is coupled to a desktop computer system.

DETAILED DESCRIPTION

An optical apparatus and method is described for surface detection of a magnetic disk. In the following description, numerous specific details are set forth such as particular elements, power levels, distances, etc., in order to provide a thorough understanding of the present invention. However, it will be obvious to one skilled in the art that the invention may be practiced without these specific details. In other instances, well known techniques, materials, components, etc., have not been shown or described in detail in order to avoid obscuring the invention.

A magnetic disk substrate should be smooth and free from defects. Unfortunately, defects are an inherent part of the manufacturing process. For example, scratches, bumps, voids, or contaminate particles such as dust may be produced or end up being deposited at various locations on the disk's surface. To properly certify the quality of the disk surface, these imperfections must be qualified and quantified. The type of various defects should also be differentiated. For instance, it is important to know whether the defect is a protrusion (i.e., protruding above the disk surface) or a void (i.e., extending below the disk surface). In general, the latter type of defect is more acceptable since voids normally do not interfere with the flying of the head.

With reference to FIG. 1, there is shown a diagram of a single-beam interferometer 10 that provides both phase and amplitude detection according to the present invention. Interferometer 10 comprises a laser 12 that produces single wavelength light beam 20. In one embodiment, an ordinary helium-neon laser is used which outputs a coherent light beam having a wavelength of 6326Å. The output power of the helium-neon laser is approximately 15 milliwatts. Light beam 20 is passed through a spatial filter 13 to eliminate unwanted signal noise.

After filtering, the light beam is split into components 11 and 22 utilizing beam splitter 14. In one implementation, beam splitter 14 comprises a 50% mirror that separates the light beam into the 11 and 22 components. Ordinary mirrors 17 & 15 and lenses 18 & 19 orthogonally direct the respective 11 and 22 light beam components into prism 21. The two light beam components are recombined in prism 21 where an interference occurs.

The present invention utilizes a phase/contrast method of observation in which phase changes introduced by a defect present in the magnetic disk are transformed into changes in intensity. The intensity of any point of the image plane is directly proportional to the phase change due to the corresponding element of the defect present on the surface of the magnetic disk.

With continuing reference to FIG. 1, the interference pattern generated by prism 21 is shined through a retardation plate 24 and an ordinary beam expander 25. The interference pattern incident on the retardation plate 24 is resolved into two linearly polarized components which vibrate perpendicular to each other and travel with different velocities in the plate. The beams emerge from plate 24 with a phase delay. The phase delay or retardation is dependent on the bi-refringent characteristics of the particular crystal which comprises plate 24. In one embodiment of the present invention, a quarter-waveplate (available from Karl Lambrecht Corporation of Chicago, Ill.) is utilized. The result is a circularly polarized light beam emergent from plate 24.

Practitioners in the relevant art will understand that when the phase information of the interference pattern is retarded (with respect to the diffraction spectra) regions with defects will have greater optical thickness. The greater optical thickness means that a brighter illumination will be produced, thereby resulting in bright phase contrast. That is, retardation plate 24 may be utilized in accordance with the present invention to increase the optical resolution of the system. It should be understood, however, that use of a retardation plate 24 is an option that is specific to the embodiment of FIG. 1. In other words, retardation of the interference pattern is not deemed essential to the interferometer of the present invention. Alternative embodiments need not include retardation plate 24.

Following introduction of a phase delay into the interference pattern, beam expander 25 directs the component light beams toward magnetic disk 30 in a direction that is substantially orthogonal to the surface of the disk.

Positioned between beam expander 25 and magnetic disk 30 is a cylindrical lens 26. Cylindrical lens 26 has the property of magnifying in one direction only and is employed to generate a line of light from the circular beam emergent from retardation plate 24 and beam expander 25. The linear light pattern generated by cylindrical lens 26 is projected onto a portion of disk 30. For example, in one implementation, cylindrical lens 26 projects a line of light extending in a radial direction from an inside diameter 33 to an outside diameter 34 of disk 30. This aspect of the invention is shown in FIG. 2, where the line of light generated by cylindrical lens 26 appears as illumination pattern 50. As will be discussed in more detail below, disk 30 can be rotated about its central axis 31 to completely map an annular area of disk 30 extending from inside diameter 33 to outside diameter 34.

The light reflected off the surface of magnetic disk 30 is projected onto a linear detection array 45 utilizing an ordinary 50% mirror 29. Detection array 45 may comprise a linear array of photodiodes or some other suitable detection device. For example, a linear detection array comprising semiconductor charged-coupled devices (CCDs) may be utilized. Linear detectors comprising CCDs fabricated from silicon (Si), germanium (Ge), or platinum silicide (PtSi) may be used. Alternatively, a commercially-available photodiode array may be employed as the detection device.

It is appreciated that each element of detection array 45 might typically have its own associated pre-amplifier, together with a multiplexed output. Photodetector arrays are well known among those skilled in the optical arts. They produce an electrical signal which varies dependent upon the intensity of the impinging light. The electrical response of detection array 45 may be calculated by integrated over the detector area.

As explained earlier, defects present on disk 30 cause variations in the intensity on the reflected light beam. These variations are translated into differences in the strength of the electrical signal output by detection array 45. Hence, the line of light reflected off the surface of the magnetic disk has an intensity that varies dependent on the presence, location and type of defects that exist. These variations are converted into an electrical signal by the linear detection array 45. The entire surface of the magnetic recording layer is inspected by simply turning the disk once about its central rotational axis. Disk 30 may be rotated using well known mechanical methods (e.g., motors, spindles, cranks, etc.).

In another embodiment of the present invention, detection array 45 is mounted to a piezotrain 40, which is attached to a magnifier 41. Piezotrain 40 functions to move magnifier 41 vertically; that is, up-and-down relative to the direction of the impinging reflected light. By moving the position of the magnifier in this manner the focal distance of the light beam components is changed. This allows topographical features of the disk surface to be distinguished.; for example, surface voids or pits can be distinguished from protrusions or bumps, etc. In other words, whether the defect extends above or below the surface of the disk is determined by repeatedly inspecting the output of array 45 at different vertical or "z" positions of magnifier 41. This aspect of the inspection apparatus of the present invention provides a valuable advantage over prior art systems that are incapable of such classifications.

It should be understood, of course, that piezotrain 45 may be substituted with any ordinary mechanical device capable of displacing magnifier 41 in a vertical (i.e., up-and-down) direction. Likewise, instead of moving a magnifier, detection array 45 may be moved up-an-down to vary the optical distance to achieve the same result.

The entire inspection process, including operation of piezotrain 40, may be controlled by a computer coupled with detection array 45. In this way, light intensity information across the entire surface of the magnetic disk can be automatically recorded and processed to produce a map of the size, location and type of defects present on the surface of the disk. Such a system is illustrated in FIG. 3 wherein array 45 is coupled to an ordinary computer system 60 having a display monitor 61 via line 47. For example, a variety of ordinary software programs may be utilized to provide a 3-dimensional visual display of the defects present on a given disk. A typical system configuration would include a controller, a computer interface board and software for performing the measurements at a particular location on the disk. To map the entire recording surface, the disk may be slowly turned while the inspection process continues. At the same time, piezotrain 45 may be utilized to differentiate defects as being protrusions or voids.

Instead of continuously rotating the disk during the inspection process, another possibility is to perform inspection at discrete annular positions of the disk. In such a scheme, the annular position of the disk remains fixed while inspection data is gathered. The disk is then rotated to a new annular position and the inspection process repeated until the entire surface has been mapped. Regardless of the manner that inspection data is obtained, the method of the present invention still only requires a single rotation of the disk to map the full recording surface.

We claim:

1. Apparatus for surface inspection of a magnetic disk comprising:
   a light source providing a single wave length light beam;
   optical means for generating an interference pattern from the light beam;
   a cylindrical lens arranged to project the interference pattern onto a surface of the magnetic disk as a line of light extending radially from an inside diameter to an outside diameter of the magnetic disk; and
   a photo detector array positioned to convert a reflection of the line of light from the surface of the magnetic disk into an electrical signal having a magnitude that depends upon reflected light intensity, wherein a defect on the surface of the magnetic disk causes a variation in the reflected light intensity.

2. The apparatus of claim 1 further comprising a retardation plate creating a phase shift in the interference pattern.

3. The apparatus of claim 2 further comprising a beam expander positioned between the retardation plate and the cylindrical lens.

4. The apparatus of claim 2 further comprising:
   a magnifier; and
   a means attached to the magnifier for moving the magnifier along an axis substantially parallel to the reflection to the line of light so as to vary a focal point of the reflection.

5. The apparatus of claim 2 further comprising:
   a means for moving the photo detector array along an axis substantially parallel to the reflection to the line of light so as to vary an optical distance between the photo detector array and the surface of the magnetic disk.

6. The apparatus according to claim 1 further comprising means for rotating the magnetic disk.

7. The apparatus of claim 1 wherein the photo detector array comprises a linear array of charged-coupled devices.

8. The apparatus of claim 2 further comprising a spatial filter disposed before the optical means for filtering the single wavelength light beam.

9. The apparatus of claim 1 wherein the optical means comprises:
   a beam splitter positioned to split the light beam into first and second components;
   a prism;
   a plurality of mirrors that project the first and second components into the prism along orthogonal axes, thereby generating the interference pattern.

10. The apparatus of claims 1, 2, 3, 4, 5, 6, 7, 8 or 9 further comprising data processor means coupled with the photo detector array for processing the electrical signal to produce a digital map of the surface of the magnetic disk.

11. A method for surface inspection of a magnetic disk comprising the steps of:
   (a) generating an interference pattern characterized by a phase shift from a laser beam;
   (b) projecting the interference pattern through a cylindrical lens onto a surface of the magnetic disk as a linear beam;
   (c) detecting a reflection of the linear beam from the surface with a linear detector array, the linear detector array outputting an electrical signal which varies in magnitude depending upon the reflected linear beam intensity, wherein a defect on the surface of the magnetic disk is characterized by a signature light intensity variation in the reflected linear beam.

12. The method according to claim 10 wherein step (a) comprises the steps of:
   splitting the laser beam into first and second components;
   recombining the first and second components in a prism wherein interference occurs.

13. The method according to claim 12 further comprising the step of:
   shinning the interference pattern through a retardation plate.

14. The method according to claim 13 wherein the retardation plate comprises a quarter-wave retardation plate.

15. The method according to claim 13 further comprising the step, prior to step (b), of:
   passing the interference pattern through a beam expander.

16. The method according to claim 11 wherein the linear beam is projected onto the surface extending from an inside diameter to an outside diameter of the magnetic disk.

17. The method according to claim 16 further comprising the step of:
   rotating the magnetic disk by 360 degrees about a central rotational axis such that the reflection of the interference pattern is detected for an annular area of the magnetic disk bounded by the inside and outside diameters.

18. The method according to claim 11 further comprising the initial step of:
   spatially filtering the laser beam.

19. The method according to claim 11, 12, 13, 14, 15, 16, 17 or 18 wherein the reflection is projected in a first direction, further comprising the step of:
   moving a magnifier positioned above the linear detector array so as to distinguish the defect as being either a void or a protrusion.

20. The method according to claim 19 further comprising the step of:

processing the electrical signal to map the size and location of the defect.

21. An interferometer for inspecting a surface of a disk comprising:

a laser providing a beam of coherent light;

optics for generating an interference pattern from the beam;

a lens arranged to project the interference pattern onto the surface of the disk as a line of light;

a detection array positioned to convert a reflection of the line of light from the surface of the disk into an electrical signal having a magnitude that varies dependent upon reflected light intensity, wherein an imperfection on the surface of the disk causes a variation in the reflected light intensity;

means for changing an optical focal distance between the detection array and the surface of the disk such that the defect can be classified as being of a certain type.

22. The interferometer of claim 21 further comprising a retardation plate positioned between the optics and the lens such that the interference pattern passes through the retardation plate, emerging with a phase shift.

23. The interferometer of claim 22 further comprising means for rotating the disk at least once about a central rotational axis.

24. The interferometer of claim 23 further comprising a beam expander positioned between the retardation plate and the lens.

25. The interferometer of claim 21 wherein the detection array comprises a linear array of charged-coupled devices.

26. The interferometer of claim 21 wherein the detection array comprises a linear array of photodiodes.

27. The interferometer of claim 21 further comprising a spatial filter disposed before the optical means for filtering the single wavelength light beam.

28. The interferometer of claims 21, 22, 23, 24, 25, 26, or 27 further comprising a computer coupled with the detection array, the computer processing the electrical signal to produce a digital map of the surface of the disk.

* * * * *